(12) United States Patent
Urban (10) Patent No.: US 11,730,623 B2
(45) Date of Patent: Aug. 22, 2023

(54) MANDIBLE SUPPORT DEVICE FOR USE WITH A POSITIVE AIRFLOW PRESSURE DEVICE

(71) Applicant: Amy Dianne Urban, Austin, TX (US)

(72) Inventor: Amy Dianne Urban, Austin, TX (US)

( * ) Notice: Subject to any disclaimer, the term of this patent is extended or adjusted under 35 U.S.C. 154(b) by 252 days.

(21) Appl. No.: 16/859,839

(22) Filed: Apr. 27, 2020

(65) Prior Publication Data

US 2020/0253778 A1 Aug. 13, 2020

Related U.S. Application Data

(63) Continuation of application No. 16/272,842, filed on Feb. 11, 2019, now abandoned.

(60) Provisional application No. 62/658,953, filed on Apr. 17, 2018.

(51) Int. Cl.
| | | |
|---|---|---|
| *A61F 5/00* | (2006.01) | |
| *A61F 5/56* | (2006.01) | |
| *A61C 7/08* | (2006.01) | |
| *A61M 16/06* | (2006.01) | |

(52) U.S. Cl.
CPC .............. *A61F 5/566* (2013.01); *A61C 7/08* (2013.01); *A61M 16/06* (2013.01); *A61M 2210/0625* (2013.01)

(58) Field of Classification Search
CPC ... A61F 5/37; A61F 5/56; A61F 5/566; A61C 7/08; A61M 16/06; A63B 71/085
USPC ................. 128/848, 859, 861, 862
See application file for complete search history.

(56) References Cited

U.S. PATENT DOCUMENTS

| | | | |
|---|---|---|---|
| 3,381,377 A | | 5/1968 | Grayson |
| 4,568,280 A | * | 2/1986 | Ahlin ...................... A61F 5/566 |
| | | | 433/6 |
| 5,313,960 A | | 5/1994 | Tomasi |
| 5,636,379 A | * | 6/1997 | Williams ............. A63B 71/085 |
| | | | 128/862 |
| D685,098 S | | 6/2013 | Tompkins |
| 8,620,045 B2 | | 12/2013 | Adams |
| 9,161,824 B2 | | 10/2015 | Chishti et al. |
| 2004/0007239 A1 | * | 1/2004 | Eubank .................... A61C 7/08 |
| | | | 128/861 |
| 2010/0263677 A1 | | 10/2010 | Thornton |
| 2011/0005531 A1 | | 1/2011 | Manzo |

(Continued)

OTHER PUBLICATIONS

Simmons et al., "Benefits of Mandibular Stabilization via Combination Therapy," Sleep Review, <http://www.sleepreviewmag.com/2017/06/mandibular-stabilization-combination-therapy/> dated Jun. 15, 2017.
Airway Management, "TAP PAP CS," <http://tapintosleep.com/dentist/products/tap-pap-cs/> webpage publicly available at least as early as Oct. 23, 2017.

(Continued)

*Primary Examiner* — Adam Baker
(74) *Attorney, Agent, or Firm* — Michael Best & Friedrich LLP (57) ABSTRACT

A mandible support device for use with the maxillary teeth and mandibular teeth of a patient includes a first tray configured to engage one or more of the maxillary teeth, a second tray configured to engage one or more of the mandibular teeth, and a spacer having a body with a first surface and a second surface opposite the first surface. The first surface is coupled to the first tray and the second surface is coupled to the second tray. The spacer is configured to position the first tray and the second tray in a centric occlusion orientation.

8 Claims, 7 Drawing Sheets

(56) References Cited

U.S. PATENT DOCUMENTS

| | | | |
|---|---|---|---|
| 2011/0094522 A1* | 4/2011 | Weisflog | A61C 7/36 |
| | | | 128/861 |
| 2011/0168188 A1* | 7/2011 | Moore | A61M 16/0493 |
| | | | 128/848 |
| 2011/0201970 A1* | 8/2011 | Boyd, Sr. | A61F 5/566 |
| | | | 600/590 |
| 2013/0167846 A1* | 7/2013 | Hurley | A63B 71/085 |
| | | | 128/861 |
| 2015/0031994 A1* | 1/2015 | Straatmann | A63B 71/085 |
| | | | 600/407 |
| 2015/0136147 A1* | 5/2015 | Lucas | A61C 7/08 |
| | | | 128/861 |
| 2018/0071134 A1* | 3/2018 | Honig | A61F 5/566 |
| 2019/0083212 A1 | 3/2019 | Cowburn et al. | |

OTHER PUBLICATIONS

Universal Orthodontic Lab, "Mandibular Repositioner," <https://uniortholab.com/us/portfolio-item/mandibular-repositioner-2/> webpage publicly available at least as early as Feb. 28, 2018.

Dentsply Sirona, "Positioners," <https://www.dentsplysirona.com/en-us/solutions/topics/ortholab/products/Positioners.html> webpage believed to be publicly available at least as early as Feb. 10, 2019.

Patterson Dental, "Patterson Mouthguard EVA Material—Vacuum Forming, Clear, 5" x 5", 25/Pkg—Patterson Dental Supply," <https://www.pattersondental.com/Supplies/ProductFamilyDetails/PIF_74567> webpage believed to be publicly available at least as early as Feb. 10, 2019.

Slidewell Laboratories, "Silent Nite sl," <https://glidewelldental.com/services/dental-sleep-medicine/silent-nite-sl> webpage publicly available at least as early as Jun. 26, 2017.

* cited by examiner

MANDIBLE SUPPORT DEVICE FOR USE WITH A POSITIVE AIRFLOW PRESSURE DEVICE

CROSS-REFERENCE TO RELATED APPLICATIONS

This application claims priority to U.S. Provisional Patent Application No. 62/658,953, filed Apr. 17, 2018 and U.S. Non-Provisional patent application Ser. No. 16/272,842, filed Feb. 11, 2019, the entire contents of which are incorporated herein by reference.

BACKGROUND

The present disclosure relates to a mandible support device, and more specifically to a mandible support device for use with a positive airflow pressure (PAP) device.

Posterior movement of the mandible and oral structures generally presents a restriction to the airway. During sleep, this can cause and/or contribute to a hypopneic or other obstructive sleep condition. Currently, external chin straps are used to stabilize the mandible to reduce or prevent such occurrences. External straps, however, are uncomfortable to wear, unsightly, and ineffective. Furthermore, positive airway pressure therapy for obstructive sleep apnea can cause opening of the mouth which diminishes the seal and increases air leakage of positive airway pressure devices.

SUMMARY

In one aspect, an assembly for use with a patient having an obstructive sleep condition includes an air pump configured to provide positive pressure air, a mask configured to receive air from the air pump, and a mandible support device. The mandible support device includes a first tray having a base wall configured for placement adjacent the occlusal surfaces of one or more maxillary teeth of the patient, a front wall configured for placement adjacent the facial surfaces of one or more maxillary teeth of the patient, and a rear wall configured for placement adjacent the lingual surfaces of one or more maxillary teeth of the patient. The front wall is between approximately 0.6 mm and approximately 1.1 mm thick. The mandible support device further includes a second tray and a spacer having a body with a first surface and a second surface opposite the first surface. The first surface is coupled to the first tray and the second surface is coupled to the second tray.

In another aspect, a mandible support device for use with the maxillary teeth and mandibular teeth of a patient includes a first tray configured to engage one or more of the maxillary teeth, a second tray configured to engage one or more of the mandibular teeth, and a spacer having a body with a first surface and a second surface opposite the first surface. The first surface is coupled to the first tray and the second surface is coupled to the second tray. The spacer is configured to position the first tray and the second tray in a centric occlusion orientation.

In another aspect, a method of manufacturing a mandible support device includes forming a first tray configured to engage one or more maxillary teeth of a patient, forming a second tray configured to engage one or more mandibular teeth of the patient, coupling a base wall of the first tray configured for placement adjacent the occlusal surfaces of one or more maxillary teeth to a first surface of a spacer, and coupling a base wall of the second tray configured for placement adjacent the occlusal surfaces of one or more mandibular teeth to a second surface of the spacer. A normal to the first surface of the spacer is directionally opposite to a normal of the second surface of the spacer.

In another aspect, a mandible support device for use with the maxillary teeth and mandibular teeth of a patient includes a first tray configured to engage one or more of the maxillary teeth, a second tray configured to engage one or more of the mandibular teeth, and a spacer means configured to position the first tray relative to the second tray in a centric occlusion orientation.

Other aspects of the disclosure will become apparent by consideration of the detailed description and accompanying drawings.

DETAILED DESCRIPTION

Before any embodiments of the disclosure are explained in detail, it is to be understood that the disclosure is not limited in its application to the details of the formation and arrangement of components set forth in the following description or illustrated in the accompanying drawings. The disclosure is capable of supporting other implementations and of being practiced or of being carried out in various ways.

This disclosure generally relates to a PAP device including a mandible support device positionable completely within the mouth of a patient to promote positive airway pressure therapy. More specifically, the mandible support device is configured to internally support and maintain the mandible in a substantially centric occlusion position relative to the maxilla while simultaneously allowing the patient to form a lip seal thereover. This position helps support the mandible and stops the tongue from falling back and closing off the airway while not requiring the user to use a dental deprogrammer following use of the device. The support device includes a first or mandibular tray, a second or maxillar tray, and a spacer positioned between and coupled to both the first tray and the second tray to generally maintain the centric occlusion orientation therebetween. The spacer is also configured to form a gap between the first tray and the second tray through which the patient may breathe during use. During use, the mandible support device is able to stabilize the jaw and fix the upper and lower arches together internally, providing a ligature to bone via the teeth. By operating internally via the teeth, the proposed mandible support device is able to provide more stable and predictable mandible support than doing so externally via soft tissues (e.g., via a strap).

Figure 11:
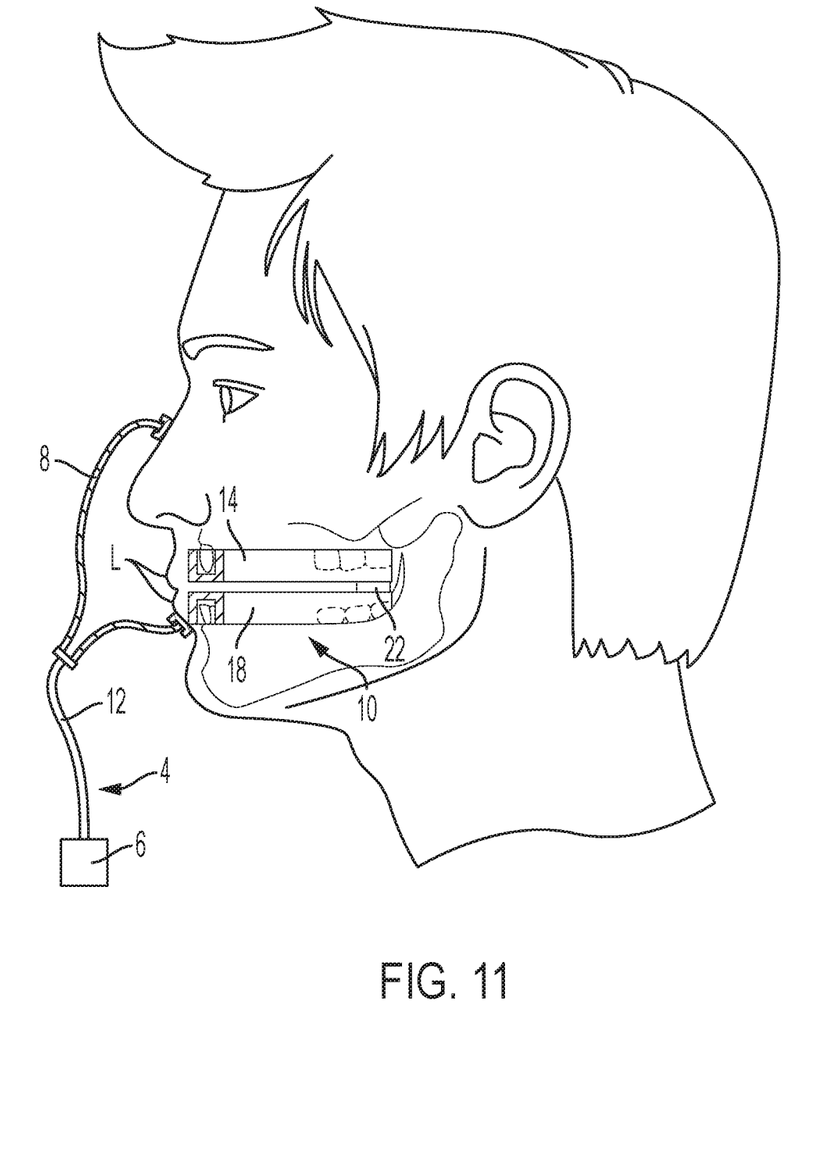
FIG. 11 is a schematic view of the mandible support device positioned within a patient's mouth with a lip seal formed and PAP machine in use.

FIGS. 1-9 illustrate a PAP device 4 including an air pump assembly 6, a facial mask 8 in fluid communication with the air pump assembly 6, and an internal mandible support device (MSD) 10. The air pump assembly 6 operates as is well known in the art providing a flow of air to the mask 8 via a hose 12. The mask 8, in turn, is configured to direct the flow of air into the patient's respiratory system. As shown in FIG. 11, the mask 8 may include a facial mask that encompasses the patient's nose and mouth forming a seal against the patient's face. The mask 8 also includes one or more straps (not shown) extending around the patient's head to secure the mask 8 against the patient's face. The straps, in turn, may be elastic or fabric with adjustable elements built therein. In other implementations, the mask 8 may include a nose plug (e.g., just be in communication with the patient's nose) or the like.

The MSD 10 is configured to support and maintain a patient's mandible relative to the maxilla in a substantially centric occlusion position without producing orthodontic movement. Specifically, the MSD 10 does not allow the mandible to be advanced beyond the centric occlusion position. The MSD 10 is positionable completely within the patient's mouth (e.g., no elements of the MSD 10 extend beyond the patient's lip seal) and sized such that the patent may form and maintain a lip seal while the MSD 10 is positioned therein. In the illustrated implementation, the MSD 10 includes a first tray 14, a second tray 18, and a spacer 22 positioned between and coupled to both the first tray 14 and the second tray 18. The first tray 14 and second tray 18 are affixed to each other in such a way, using the spacer 22, to support the mandible, preventing a retruded position and also encouraging the tongue to relax. The stabilized mandible and relaxed tongue prevent oropharyngeal structures from collapsing thus keeping airways patent. The fit of the affixed trays 14, 18, also serve to keep the jaw closed during sleep.

Figure 9:
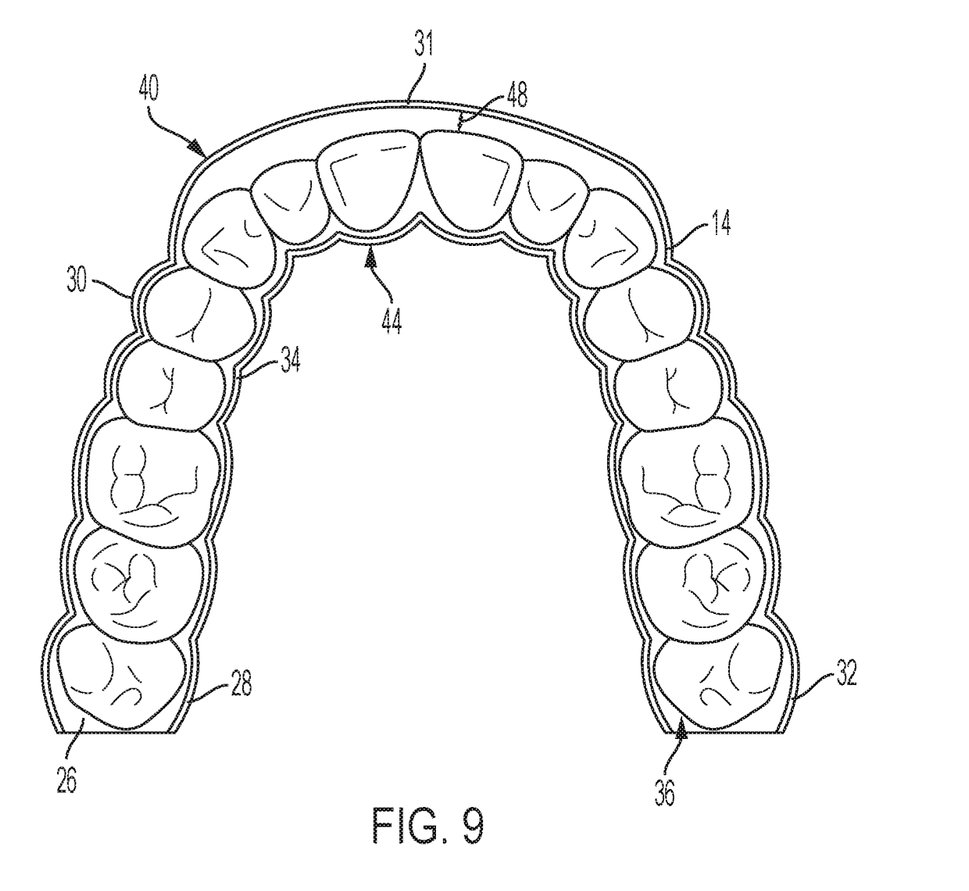
FIG. 9 is a plan view of the first tray with maxillary teeth positioned therein.

The first tray 14 of the MSD 10 is a dental tray configured to be removably secured to the maxilla such that the two become temporarily fixed relative to one another and move together as a unit. More specifically, the first tray 14 includes a substantially "U" shaped body 24 having a first end 28, a second end 32 opposite the first end 28, and a midpoint 31 positioned midway between the first end 28 and the second end 32. The body 24, in turn, includes a base wall 26, a front wall 30 extending from the base wall 26, and a rear wall 34 spaced from the front wall 30 and also extending from the base wall 26. Together, the three walls 26, 30, 34 generally form a "U" shaped channel 36 extending along the length of the body 24 between the first end 28 and the second end 32, which can be placed over the individual maxillary teeth and temporarily retained thereon. As shown in FIG. 9, when being worn, the patient's molars are generally positioned proximate the first and second ends 28, 32 while the patient's incisors are generally positioned proximate the midpoint 31. One example of the first tray 14 may include, but is not limited to, an ESSIX™ orthodontic retainer. Furthermore, the first tray 14 may be formed from, but is not limited to, BIACRYL™, INVISACRYL™, DURAN™, hardcast material, and the like.

In the illustrated implementation, the first tray 14 is molded or otherwise formed specifically to the patent's teeth such that the front wall 30 engages the facial surface of one or more of the maxillary teeth, the base wall 26 engages the occlusal surface of one or more of the maxillary teeth, and the inner wall 34 engages the lingual surface of one or more of the maxillary teeth. Furthermore, the molding process also causes the outer surfaces 38, 40, 44 of each wall 26, 30, 34, respectively, to have a curvature that substantially corresponds with the curvature of the corresponding maxillary tooth surfaces (see FIGS. 9-10). While the illustrated tray 14 is shown in direct contact with the patient's maxillary teeth, it is to be understood that in alternative implementations the tray 14 may be adjusted to compensate for other orthodontic elements such as, but not limited to, braces, retainers, fillings, and the like.

As shown in FIGS. 1-6, the walls 26, 30, 34 of the first tray 14 are formed from relatively thin material between approximately 0.4 mm and approximately 1.1 mm in thickness. In other implementations, the wall is between approximately 0.6 mm and approximately 1.1 mm in thickness. By having relatively thin walls 26, 30, 34, the outer surface 40 of the front wall 30 remains as close to the facial surface of each maxillary tooth as possible minimizing any displacement of the upper lip (L) therefrom (see FIG. 11). Stated differently, the front wall 30 of the first tray 14 does not displace the patient's upper lip more than approximately 1.1 mm from the facial surface of the corresponding maxillary tooth. The close proximity of the upper lip and maxillary teeth allow the patient to more easily form a lip seal when using the MSD 10.

In some implementations, the front wall 30 of the first tray 14 may be displaced from and not engage one or more of the maxillary teeth to form one or more gaps 48 therebetween (see FIG. 9). In such implementations, the one or more gaps 48 do not allow forces to be transmitted between the tray 14 and the corresponding tooth or teeth. For example, as shown in FIG. 9, the front wall 30 is displaced such that a gap 48 extends between the left and right canine teeth (e.g., the gap 48 is positioned between the facial surfaces of both canine teeth, both lateral incisors, and both central incisors and the front wall 30). In such implementations, forces are not transmitted between the tray 14 and that particular subset of teeth but are rather only transmitted to those teeth where the gap 48 is not present and contact between the front wall 30 and certain teeth exists. As such, the inclusion of one or more gaps 48 in the first tray 14 allows the user to specify which subset of teeth bear the forces exerted against the first tray 14.

While the present application illustrates the use of a gap 48 between the front wall 30 and corresponding facial surfaces of the teeth, it is to be understood that the first tray 14 may include gaps 48 between other specific subsets of teeth (e.g., molars, premolars, and the like) and/or between other combinations of walls (e.g., base wall 26, rear wall 34, and the like) and/or tooth surfaces (e.g., occlusal surface, lingual surface, and the like). To produce the gaps 48, a piece of material is positioned between the teeth the user wishes to block out and the corresponding wall of the tray 14 during the molding process. Once the material of the tray 14 hardens, the material is removed and the gap 48 remains.

Figure 10:
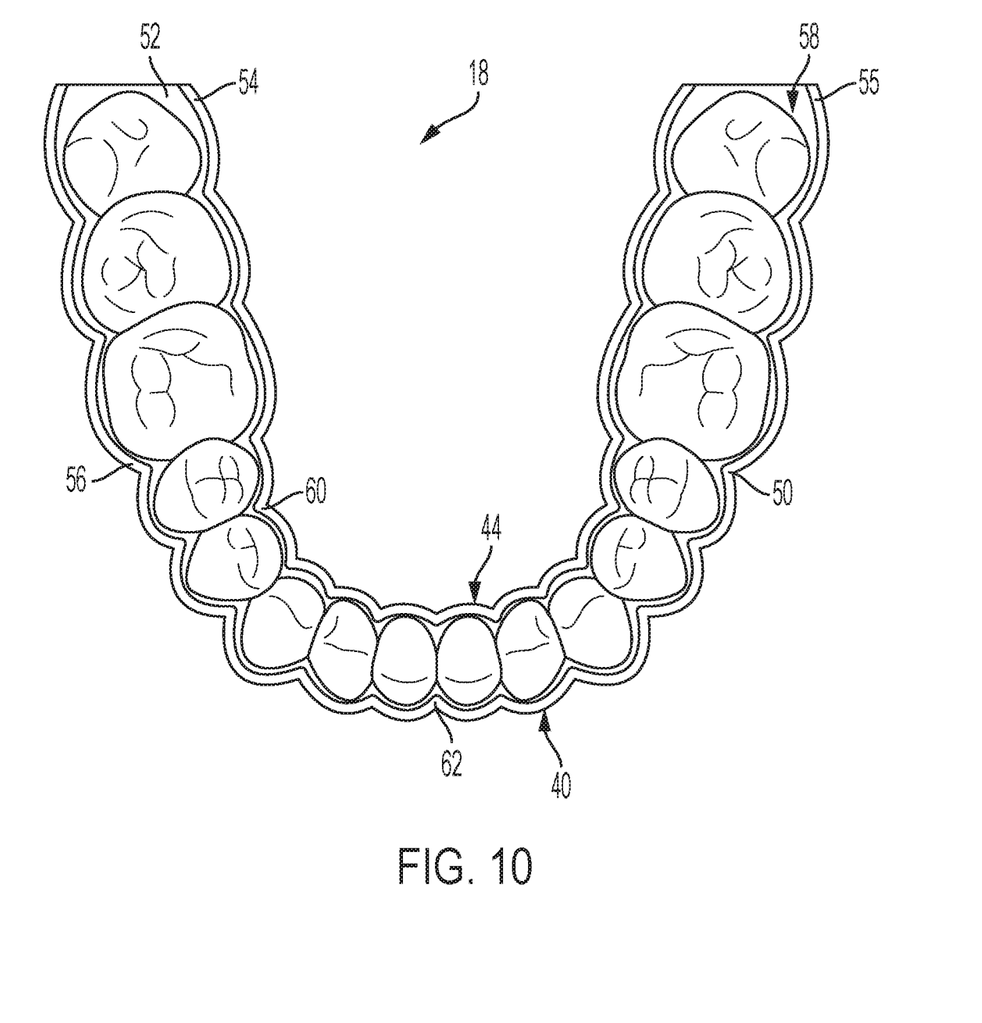
FIG. 10 is a plan view of the second tray with mandibular teeth positioned therein.

As shown in FIG. 9, the size of the gap 48 is sufficiently large so that no force is applied to the facial surface of the desired tooth during use while also being as small as possible to minimize the displacement of the patient's lips (L) and allow for a lip seal to be formed (see FIG. 10). In the illustrated implementation, the size of the gap 48 is between approximately 1 mm and approximately 2 mm.

In other implementations, portions of the tray 14 may be removed instead of creating such a gap 48. For example, the portion of the front wall 30 where the gap 48 is located in FIG. 9 may be removed from the tray 14 completely so that it no longer exists at that location. Still further, entire sections of the tray 14 may also be removed in such instances so that instead of forming a single continuous tray as is shown, the tray 14 may include two or more subportions.

Figure 6:
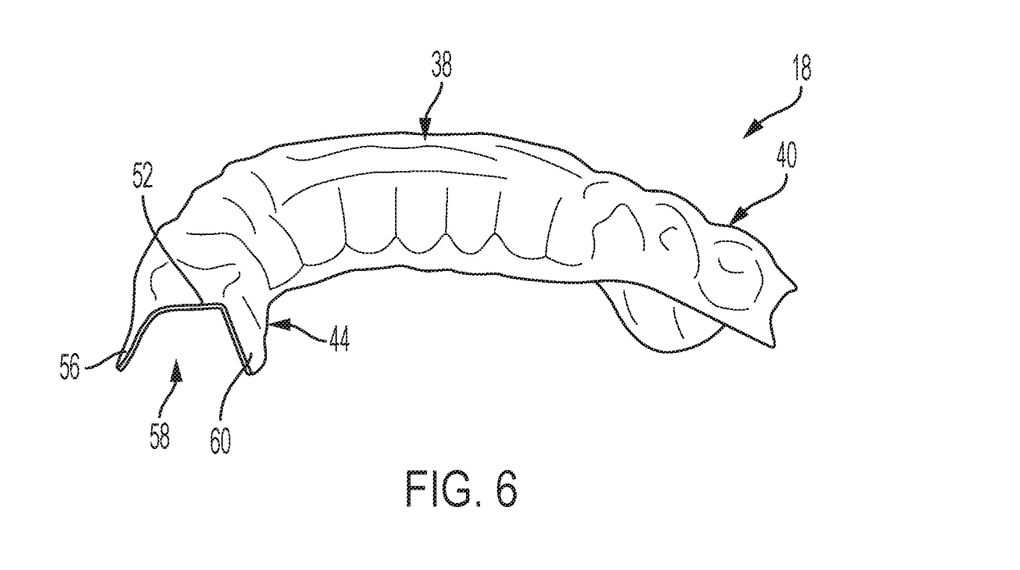
FIG. 6 is a perspective view of a second tray of the mandible support device of FIG. 1.
Figure 7:
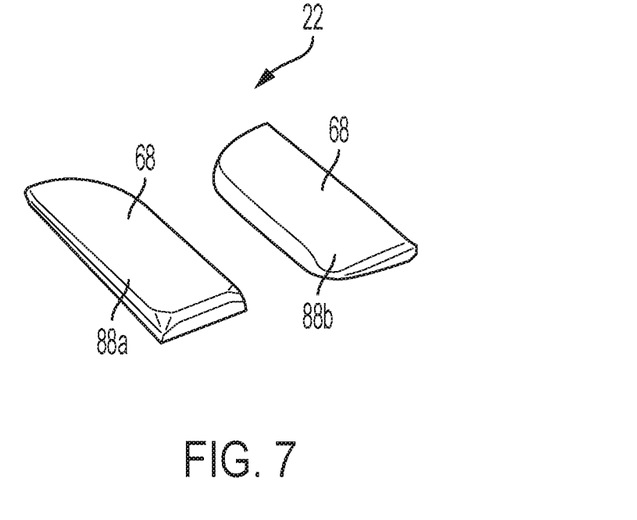
FIG. 7 illustrates one implementation of the spacer of the mandible support device of FIG. 1.
Figure 8:
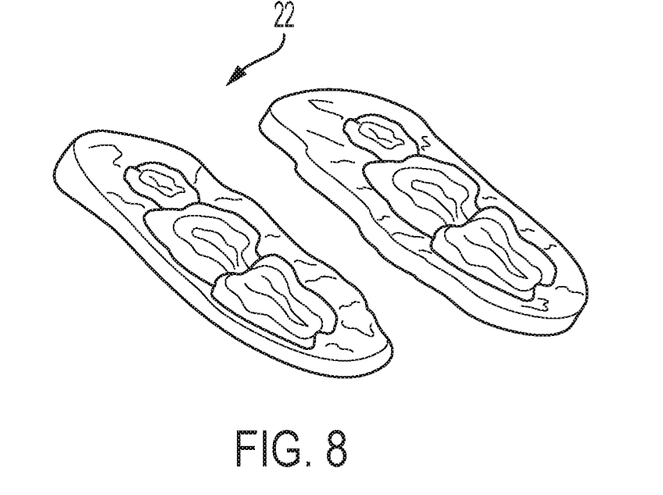
FIG. 8 illustrates another implementation of the spacer of the mandible support device of FIG. 1.

As shown in FIGS. 6 and 10, the second tray 18 of the MSD 10 is a dental tray configured to be removably secured to the mandible such that the two become temporarily fixed relative to one another and move together as a unit. The second tray 18 is substantially similar to the first tray 14 and therefore only the differences will be discussed herein. The second tray 18 includes a substantially "U" shaped body 50 having a first end 54, a second end 55 opposite the first end 54, and a midpoint 62 positioned midway between the first end 54 and the second end 55. The body 50, in turn includes a base wall 52, a front wall 56 extending from the base wall 52, and a rear wall 60 spaced from the front wall 52 and also extending from the base wall 52. Together, the three walls 52, 56, 60 generally form a "U" shaped channel 58, which can be placed over the individual mandibular teeth and temporarily retained thereon. In the illustrated implementation, the second tray 18 is molded or otherwise formed specifically to the patient's teeth such that the front wall 56 is generally in contact with and corresponds to the facial surface of one or more of the mandibular teeth, the base wall 52 is generally in contact with and corresponds to the occlusal surface of one or more of the mandibular teeth, and the inner wall 60 is generally in contact with and corresponds to the lingual surface of one or more of the mandibular teeth. The second tray 18 may also include one or more gaps 48 as described above.

While each tray 14, 18 is illustrated having a front, base, and rear wall, it is to be understood that in alternative implementations the trays 14, 18 may include some subset of walls. Furthermore, while the illustrated trays 14, 18 encompass the entire mouth (e.g., from molar to molar), first and second trays may be configured to overlie only one or one or more subsets of teeth in alternative implementations. In still other implementations, the trays 14, 18 may also be used for orthodontic movement while being used for the purpose of mandibular stabilization.

The spacer 22 of the MSD 10 is positioned between and coupled to both the first tray 14 and the second tray 18. The spacer 22 includes a body 64 having a first surface 68 in contact with and coupled to all or portions of the base wall 26 of the first tray 14, and a second surface 72 in contact with and coupled to all or portions of the base wall 52 of the second tray 18. The spacer 22 also defines a bite plane 84 substantially parallel to one of the first surface 68 and the second surface 72 and that passes through the body 64 thereof. In the illustrated implementation, the spacer 22 may be formed from THERMACRYL™ bite wafers, THERMACRYL™ beads, and/or EVA™ material.

Figure 1:
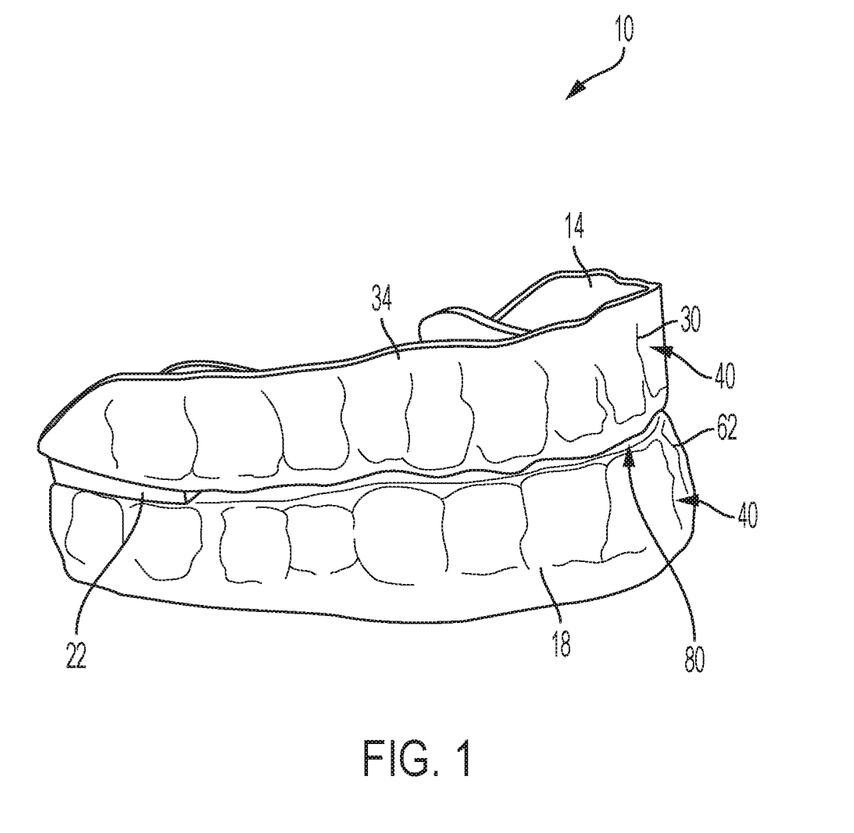
FIG. 1 is a perspective view of a mandible support device.
Figure 2:
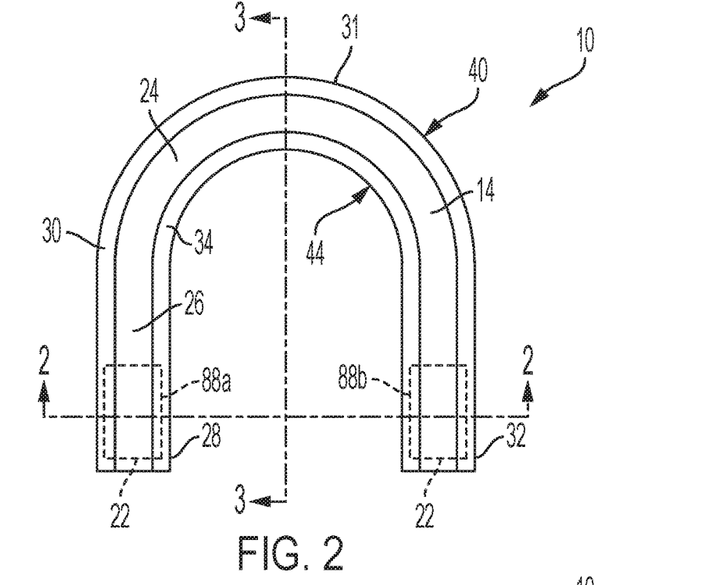
FIG. 2 is a top view of the mandible support device of FIG. 1.
Figure 3:
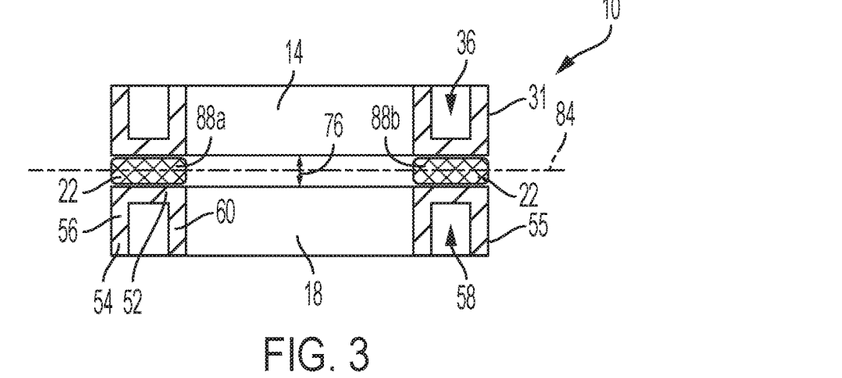
FIG. 3 is a section view of the mandible support device taken along line 2-2 of FIG. 2.
Figure 4:
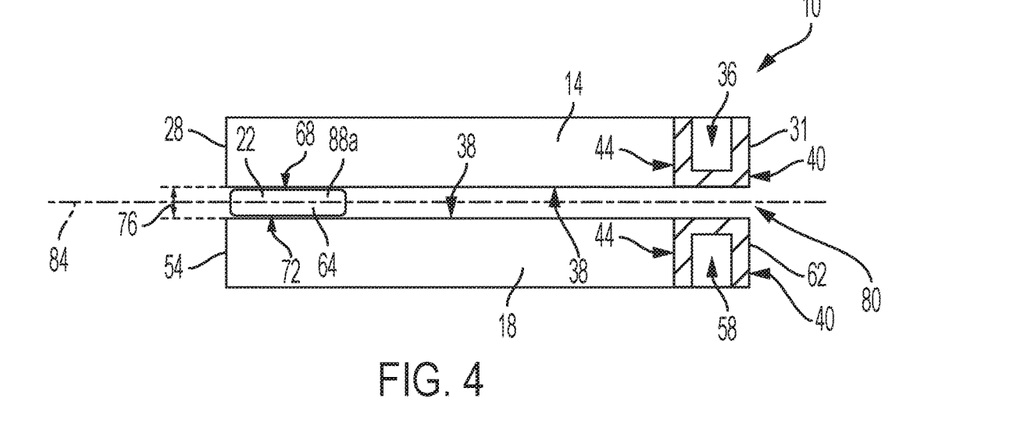
FIG. 4 is a section view of the mandible support device taken along line 3-3 of FIG. 2.
Figure 5:
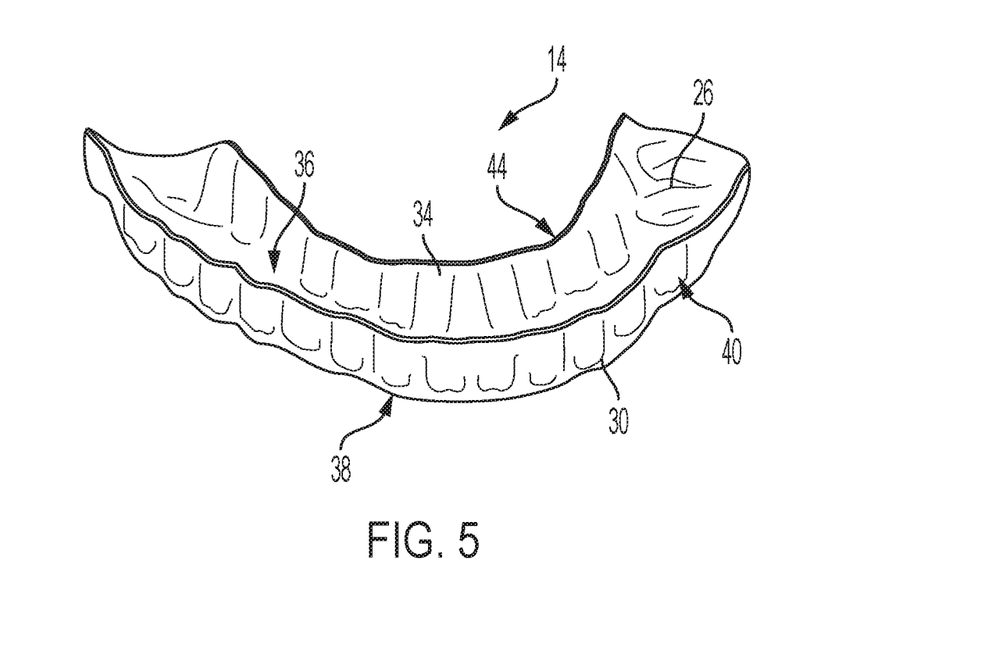
FIG. 5 is a perspective view of a first tray of the mandible support device of FIG. 1.

As shown in FIGS. 3 and 4, the first surface 68 and the second surface 72 are spaced a first distance 76 from one another generally representing the thickness of the spacer 22. In the illustrated implementation, the spacer 22 has a substantially equal thickness over its entire length such that the first surface 68 and second surface 72 are substantially parallel to one another. In alternative implementations, however, the first surface 68 may be placed at an angle relative to the second surface 72 such that the body 64 forms a wedge shape and the like (not shown) to produce different mandibular orientations relative to the maxilla.

Once assembled, the spacer 22 is configured to orient the first tray 14 a distance from and parallel to the second tray 18 to form a gap 80 therebetween. The resulting gap 80 between the first tray 14 and the second tray 18 allows air to pass between the trays 14, 18 such that the patient can breathe while wearing the MSD 10. In the illustrated implementation, the gap 80 is approximately 3 mm wide.

During use, the spacer 22 is configured to permit some relative movement between the first tray 14 and the second tray 18. More specifically, each spacer 22 is resiliently compressible such that the user can bite down onto the trays 14, 18 and cause the first distance 76 to be reduced (e.g., the first tray 14 moves closer to the second tray 18, causing the gap 80 to reduce in width). The spacer 22 is also configured to bias the two trays 14, 18 toward a rest position (i.e., the central occlusion position), such that when the trays 14, 18 vary from the rest position the spacer 22 biases the trays 14, 18 back toward the rest position. The spacer 22 is also configured to restrict the advancement of the mandible beyond (forward of) the central occlusion position. This combination of movement restrictions and allowances maintains the trays 14, 18 in a centric occlusion orientation while granting the patient some small adjustment capabilities to increase comfort.

In the illustrated implementation, the spacer 22 includes a thermoplastic wafer formed from compressible material. More specifically, the spacer 22 includes two bodies 88a, 88b, each coupled to both the first tray 14 and the second tray 18 proximate the molars (see FIGS. 1-4, and 11). In the illustrated implementation, the first body 88a is positioned proximate the first end 28 of the tray 14 (e.g., proximate the molars) and the second body 88b is spaced from the first body 88a and positioned proximate the second end 32 of the first tray 14. While the illustrated implementation includes two spacer bodies 88a, 88b, in other implementations other combinations, locations, and quantities of bodies may be used to position the first tray 14 relative to the second tray 18 while permitting the desired quantity of air to pass through the gap 80 for breathing.

While the illustrated spacer 22 includes two bodies 88a, 88b engaging the maxilla and mandible via a pair of trays 14, 18, it is to be understood that in some alternative implementations, the spacer 22 may engage the teeth directly via a mount attached directly thereto via orthodontic cement and the like. In such implementations, the mounts may serve to supplement or replace one or more of the trays 14, 18.

While not illustrated, the spacer 22 may also be supplemented with one or more bands or elastic elements to apply forces to one or both of the first tray 14 and the second tray 18. Such elastic elements can serve to help position the trays 14, 18 relative to one another or bias the trays 14, 18 toward a particular position.

To manufacture the MSD 10, the first tray 14 is molded to the patient's maxilla such that the walls 26, 30, 34 of the tray 14 engage the patient's maxillary teeth. As described above, molding the tray 14 to the maxillary teeth causes the outer surface 38 of the base wall 26 to produce a contour generally representative of the contour of the occlusal surfaces of the maxillary teeth (e.g., the molars). While not shown, one or more gaps 48, described above, may also be included in the first tray 14 to isolate one or more teeth therefrom.

The second tray 18 is molded to the patient's mandible such that the walls 52, 56, 60 of the tray 18 engage the patient's mandibular teeth. As described above, molding the tray 18 to the mandibular teeth causes the outer surface 38 of the base wall 52 to produce a contour generally representative of the contour of the occlusal surfaces of the mandible teeth (e.g., the molars). While not shown, one or more gaps 48, described above, may be included in the second tray 18 to isolate one or more teeth therefrom.

In some implementations, the first and second trays 14, 18 can be formed by pouring material into dental stone. In still other implementations, the trays 14, 18 may be formed using ESSIX™ trays suck down machine or lost wax denture techniques. In still other implementations, the trays 14, 18 may be formed using a scanner (not shown) configured to scan the teeth of the patient. In such implementations, sensors may also be included that are capable of detecting when the patient is clenching and which teeth are under tension. The sensors may also be able to detect the forces that are being applied to the jaw as it is attempting to drop open. Still further, the sensors may be configured to detect the ideal protrusive position that is most beneficial to the patient and airway.

The patient then forms an impression into the bodies 88a, 88b of the spacer 22 by biting down directly thereon in a relaxed manner. The biting action causes an impression of the maxillary molars to be formed on the first surface 68 of each body 88a, 88b and an impression of the mandibular molars to be formed on the second surface 72 of each body 88a, 88b with the relative positions of the two impressions corresponding with the centric occlusion position of the mouth. In alternative implementations, the patient may bite down on the spacer 22 while wearing the trays 14, 18 such that the impressions are formed on each of the elements simultaneously.

In some implementations, grooves, depressions, and/or dimples may also be formed on the trays 14, 18, and/or spacer 22, to provide extra retention capabilities to both items when being adhered together. The dimples may also serve as reference points in one or both items to more easily allow the trays 14, 18 to be aligned in the proper positions relative to the spacer 22.

Once all the elements have been formed, the contour of the outer surface 38 of the base wall 26 of the first tray 14 generally corresponds with the impression formed on the first surface 68 of the spacer bodies 88a, 88b (e.g., both generally correspond with the size and shape of the patient's maxillary molars) while the outer surface 38 of the base wall 52 of the second tray 18 generally corresponds with the impression formed on the second surface 72 of the spacer bodies 88a, 88b (e.g., both generally correspond with the size and shape of the patient's mandibular molars). Using these impressions as guides, the first and second trays 14, 18 can be attached to the spacer bodies 88a, 88b by aligning the patterns formed in each and using adhesive (e.g., cyanoacrylate) or other attachment mechanisms such as, but not limited to, fasteners, plastic welding, and the like. Since the relative positions of the impressions generally correspond with the centric occlusion position of the mouth, the first and second trays 14, 18, in turn, are coupled to the spacer 22 in the same centric occlusion orientation.

In some implementations, the MSD 10 may be formed by 3-D printing one or more of the trays 14, 18 and spacer 22.

To use the PAP device 4 in a positive airway pressure therapy session, the patient first places the MSD 10 in his or her mouth positioning the first tray 14 over the maxillary teeth so that they are at least partially positioned within the channel 36 thereof and positioning the second tray 18 over the mandibular teeth so that they are at least partially positioned within the channel 58 thereof.

As the teeth enter their respective channels 36, 58, the teeth and jaw take on the orientation established by the MSD 10 and therefore become oriented in a centric occlusion position. Once inserted, the trays 14, 18 offer enough retention to keep the mouth closed while still providing the patient with the option of mouth breathing as the MSD 10 allows air to pass between the two trays 14, 18 (e.g., through the gap 80).

With the MSD 10 inserted, the thin walls of both trays 14, 18 are configured to allow the patient to form a lip seal over the MSD 10 (e.g., such that the MSD 10 is positioned completely within the user's mouth).

With the MSD 10 in place, the patient may then position the mask 8 against his or her face forming a seal therewith. The mask 8 may then be secured in place with one or more elastic bands (not shown) extending around the patient's head. As described above, the illustrated mask 8 is shaped to encompass both the patient's mouth and nose however alternative masks may only encompass the nose. Furthermore, the MSD 10 as illustrated herein is configured so that a single MSD 10 is capable of being operated with multiple different mask designs, types, and styles. With the mask 8 in place, the patient may then initiate the therapy session by activating the air pump 6, whereby air will be supplied to the mask 8 via the hose 12. The therapy session then continues as is well known in the art with the patient maintaining a lip seal and proper mandible support through use of the MSD.

The various features of the disclosure are set forth in the following claims.

The invention claimed is:

1. A mandible support device comprising:
a first tray having a base wall configured for placement adjacent the occlusal surfaces of one or more maxillary teeth of a patient, each portion of the first tray between 0.4 mm and 1.1 mm in thickness; and
a second tray having a base wall configured for placement adjacent the occlusal surfaces of one or more mandibular teeth of the patient, each portion of the second tray between 0.4 mm and 1.1 mm in thickness,
wherein the first tray is spaced a distance from the second tray to form a gap therebetween by a spacer having a body coupled to both the first tray and the second tray, and
wherein the mandible support device is configured such that upon engagement with the patient for operable use, the spacer is located proximate maxillary molar and mandibular molar teeth of the patient and the first tray cooperates with the second tray to position the first tray and the second tray in a centric occlusion position.

2. The mandible support device of claim 1, wherein the mandible support device is configured such that upon engagement with the patient, the first and second trays bias the one or more maxillary teeth and the one or more mandibular teeth together.

3. The mandible support device of claim 1, wherein the mandible support device is configured such that upon engagement with the patient, the first and second trays permit the formation of a lip seal wholly containing the mandible support device within the mouth of the patient.

4. The mandible support device of claim 1, wherein the base wall of the first tray is coupled to the base wall of the second tray with cyanoacrylate.

5. The mandible support device of claim 1, wherein the body is a first body, and wherein the spacer further has a second body coupled to both the first tray and the second tray.

6. The mandible support device of claim 1, wherein the gap is approximately 3 mm wide.

7. The mandible support device of claim 1, wherein the spacer is configured to restrict the advancement of the mandible forward of the centric occlusion position.

8. The mandible support device of claim 1, wherein the mandible support device is configured such that upon engagement with the patient, the spacer is located proximate the rearmost maxillary molar and the rearmost mandibular molar teeth of the patient.

* * * * *